United States Patent [19]

Slivon et al.

[11] Patent Number: 4,982,097

[45] Date of Patent: Jan. 1, 1991

[54] VAPORIZATION DEVICE FOR CONTINUOUS INTRODUCTION OF LIQUIDS INTO A MASS SPECTROMETER

[75] Inventors: Laurence E. Slivon, Upper Arlington; Donald V. Kenny; Richard A. Severance, both of Columbus, all of Ohio

[73] Assignee: Battelle Memorial Institute, Columbus, Ohio

[21] Appl. No.: 354,643

[22] Filed: May 19, 1989

[51] Int. Cl.⁵ .............................................. B01D 59/44
[52] U.S. Cl. ................................ 250/288 M; 250/282; 250/281
[58] Field of Search ................ 250/288 A, 288, 282, 250/423 R, 423 F, 425, 281; 219/325, 326

[56] References Cited

U.S. PATENT DOCUMENTS

| | | | |
|---|---|---|---|
| 3,458,699 | 7/1969 | Padrta | 250/288 |
| 3,589,171 | 6/1971 | Haley | 250/288 |
| 4,122,343 | 10/1978 | Risby et al. | 250/282 |
| 4,160,161 | 7/1979 | Horton | 250/288 A |
| 4,391,778 | 7/1983 | Andresen et al. | 250/288 A |
| 4,403,147 | 9/1983 | Melera et al. | 250/288 A |
| 4,607,163 | 8/1988 | Mizuno | 250/288 |
| 4,794,252 | 12/1988 | Bateman et al. | 250/282 |
| 4,820,648 | 4/1989 | Caprioli et al. | 250/288 |
| 4,861,988 | 8/1989 | Henion et al. | 250/288 A |

*Primary Examiner*—Jack I. Berman
*Assistant Examiner*—Kiet T. Nguyen
*Attorney, Agent, or Firm*—Klaus H. Wiesmann

[57] ABSTRACT

This invention is designed to serve as an interface between a liquid chromatograph and a conventional or tandem mass spectrometer (LC/MS, LC/MS/MS). It may also be used for liquid sampling without prior separation of analytes by a liquid chromatograph. This invention differs from prior art in that vaporization of the analytical sample (LC eluent) occurs through the action of condensing pressurized steam on the exterior of a low thermal mass metal capillary, while the aqueous LC eluent is flowing through the metal capillary. The steam is obtained by heating a small volume of water sealed within the device. LC eluent entering the capillary results in localized cooling and subsequent condensation of the pressurized steam on the outer surface of the capillary. The process of condensation deposits energy to the capillary equivalent to the latent heat of vaporization of water. This energy results in flash vaporization of the LC eluent within the capillary. Condensed water flows along the outer wall of the metal capillary where it is returned to the trapped liquid reservoir for revaporization. Energy coupling to the LC eluent is substantially more efficient than methods used in prior art interface devices. This invention minimizes overheating of temperature sensitive analytes separated by the LC and rapidly self compensates for changes in eluent flow or eluent composition without the need for adjustment in operating temperature. This invention eliminates the need for aerosol desolvation prior to ionization.

28 Claims, 5 Drawing Sheets

VAPORIZATION DEVICE FOR CONTINUOUS INTRODUCTION OF LIQUIDS INTO A MASS SPECTROMETER

BACKGROUND OF THE INVENTION

The technique of combined Gas Chromatography/Mass Spectrometry (GC/MS) is considered to be the most powerful and definitive technique for the analysis of trace organics in the environment, as well as other fields such as pharmaceuticals and forensic science. Combined Liquid Chromatography/Mass Spectrometry (LC/MS) is gaining significance as a complimentary tool to GC/MS since liquid chromatography (LC) can often separate trace organics that are incompatible with gas chromatography (GC). Organic compounds for which LC provides a distinct advantage are characterized by either high molecular weight, low volatility, high polarity, sensitivity toward thermal degradation or some combination of the above. Many pharmaceuticals and toxic organic compounds fall into this classification. Conventional mass spectrometry requires that organic compounds exist in the gas phase in order to allow ionization, mass separation and detection. This requirement provides an ideal marriage between GC and MS but not between LC and MS. Although the potential for LC/MS is greater than that presently enjoyed by GC/MS, growth in LC/MS has been limited by the inherent phase incompatibility of liquid chromatography and the gas phase and vacuum requirements of mass spectrometry.

The underlying requirement of most LC/MS techniques is to transform the liquid HPLC eluent, consisting of solvent and chromatographically separated solute, into the gas phase. This transformation is necessary in order to separate the solvent from the analytically important solute, or to use the solvent vapor as a chemical ionization reagent. Additionally, most mass spectrometers and LC/MS interfaces require that the solute and solvent be present in the gas phase in order to ionize the solute and, in most cases, accommodate the vacuum requirements of the mass spectrometer. Although novel ionization techniques and ionization at atmospheric pressure have been described in conjunction with LC/MS, volatilization of the HPLC solvent remains a crucial and common feature of all LC/MS interfaces.

Reverse phase LC (mobile phase more polar than the stationary phase) is the LC method of choice for many organic compounds that are incompatible with GC. The mobile phase (eluent) is often water or a gradient mixture of water:methanol or water:acetonitrile. Water as a mobile phase or mobile phase component presents a particularly difficult problem for an LC/MS interface due to the unusually high latent heat of vaporization of water.

Most current LC/MS interface techniques operate in two steps. The first step transforms the liquid eluent into an aerosol which increases the available surface area for subsequent vaporization. The second step involves desolvation (evaporation) of the aerosol by application of heat. Many LC/MS interface techniques rely on a narrow and consistent aerosol size distribution in order to ionize the solute or electrostatically focus preformed ions immediately following the moment of complete vaporization. The close proximity in time between vaporization and ionization is often necessary in order to avoid overheating of the solute in the desolvation step. Control of the aerosol and extent of evaporation becomes difficult with gradient elution techniques because of the continuous change in solvent composition. Binary or ternary gradient elution reverse phase liquid chromatography is widely used with conventional detectors such as ultraviolet absorbance and fluorescence in order to optimize the chromatography for a particular application.

A variety of LC/MS interfaces are well-known in the patented prior art. McLafferty et al (U. S. Pat. No. 3,997,298 Dec. 14, 1976) describe a direct liquid introduction (DLI) which utilizes a restricted capillary to introduce liquid HPLC eluent directly into a heated chemical ionization source of a mass spectrometer. The solvent is vaporized in the ion source and serves as a chemical ionization reagent. This approach is limited to HPLC eluent flow rates on the order of 0.010-0.012 ml/min. Since conventional HPLC flow rates are on the order of 0.5-1.5 ml/min, the large majority of the HPLC eluent must be diverted away from the mass spectrometer.

McFadden (U.S. Pat. No. 4,055,987 Nov. 1, 1977) describes an LC/MS interface in which the liquid eluent is deposited onto a continuous moving ribbon. The ribbon passes through vacuum locks which, with the assistance of radiant heat, strip away the volatile solvent. The solutes are then thermally desorbed from the ribbon into the ion source of the mass spectrometer. A similar device has been described by Andresen et al (U.S. Pat. No. 4,740,298 Apr. 26, 1988). Although this approach can accommodate a larger fraction of conventional HPLC eluent flows than direct liquid introduction, the use of an aqueous mobile phase requires elevated temperatures which may decompose thermally sensitive compounds in the solvent stripping or thermal desorption steps.

Miyagi et al (U.S. Pat. No. 4,112,297 Sept. 5, 1978) describe the use of an ultrasonic nebulizer to convert the HPLC eluent into an aerosol. This interface provides a nebulization efficiency of 5-10 percent at an eluent flow of 1.0 ml/min. The nebulized fraction of the eluent is mixed with a carrier gas and passed through a heated cavity to evaporate the solvent component of the aerosol. The vapor phase is removed and the remaining particles are introduced into the mass spectrometer ion source.

Fite (U.S. Pat. No. 4,209,696 June 24, 1980) describe an electrospray LC/MS interface in which the HPLC eluent is passed through an electrically conductive capillary maintained at a high voltage relative to the surroundings at the exit of the capillary. This voltage causes the eluent to emerge from the capillary as fine droplets which are electrically charged. The charged droplets are passed through a heated cavity to evaporate the droplets resulting in neutral solvent vapor and ionized solute molecules.

White et al (U.S. Pat. No. 4,281,246 July 28, 1981) describe the use of a stationary tapered wire concentrator in which the eluent flows down the wire while a portion of the solvent is evaporated. The concentrated eluent is introduced into the mass spectrometer in a direct liquid introduction manner.

Takeuchi et al (U.S. Pat. No. 4,298,795 Nov. 3, 1985) describe an LC/MS interface which converts the HPLC eluent into an aerosol by nebulization with helium gas. The aerosol is optionally passed through a cavity heated at 300° C. to evaporate the solvent portion of the aerosol. The concentrated aerosol and solvent vapor are either introduced directly into the mass spectrometer ion source or passed through a jet type separator prior to the ion source in order to remove the majority of the solvent vapor.

Labowsky et al (U.S. Pat. No. 4,531,056 July 23. 1985) describe an electrospray LC/MS interface, similar to that of Fite, in which the fine droplets are desolvated by heated inert gas and ionized at atmospheric pressure.

Sakairi et al (U.S. Pat. No. 4,750,068 Feb. 11, 1986) describe an ultrasonic nebulization LC/MS interface for use with an atmospheric pressure ionization source. The nebulized aerosol is passed through a heated cavity to evaporate the solvent.

Vestal et al (U.S. Pat. No. 4,730,111 Mar. 8, 1988) describe four embodiments of a "thermospray" LC/MS interface in which solvent evaporation occurs in two steps. The first step involves partial evaporation of the HPLC eluent by passage through a heated stainless steel capillary. The second step involves passage of the aerosol through a heated cavity to complete the vaporization process. The addition or incorporation of a volatile salt such as ammonium acetate in the eluent results in an unbalanced charge on the particles as the solvent evaporates. This unbalanced charge in part results in ionization of the solute molecules. Heating of the capillary is accomplished by embedding a portion of the capillary in a heated copper block (embodiments 1 and 2), a combination of a heated copper block and electrical resistance heating of the stainless steel capillary (embodiment 3) and electrical resistance heating of the entire stainless steel capillary (embodiment 4).

Embodiment 4 is the preferred embodiment due to the low thermal mass of the stainless steel capillary. The low thermal mass of the capillary allows the interface to accommodate changing eluent composition or flow rates by alteration of the electrical power to the capillary. Although complete vaporization within the capillary can be achieved, this mode is avoided since the exit of the capillary can easily and greatly exceed the normal operating temperature of approximately 200° C. at an aqueous eluent flow of 1.0 ml/min. The nonuniformity of the capillary temperature is due to the need to provide sufficient electrical power to accommodate the high latent heat of vaporization of the aqueous mobile phase. Once the aqueous mobile phase is partially or completely vaporized, the exit region of the capillary cannot dissipate the power resulting is a dramatic rise in capillary temperature at the exit region. The resulting excessive temperature of the exit gas may result in degradation or pyrolysis of thermally sensitive solutes. A variety of temperature and flow feedback controls together with recognition of the gradient composition and rate are of critical necessity in order to control the electrical power to accommodate variations in HPLC eluent flow and eluent composition.

Several LC/MS interfaces have been described in the literature, however, most are adaptations of the above prior art and are not relevant to this invention. Two noteworthy review articles have appeared (T. R. Covey, E. D. Lee, A. P. Bruins, J. D. Henion, Anal. Chem. 1986, 58, pp. 1451A–1461A and J. B. Crowther, T. R. Covey, D. Silvestre, J. D. Henion, LC. 1985, 3, pp. 240–254) which trace the historical development of LC/MS interfaces and provide a summary of existing state-of-the art.

A further significant development is a monodisperse aerosol generation interface for LC/MS (MAGIC) (R. C. Willoughby, R. F. Browner, Anal. Chem. 1984, 56, pp. 2626–2631, and P. C. Winkler, D. D. Perkins. W. K. Williams, R. F. Browner, Anal. Chem. 1988, 60, pp. 489–493). This work describes a method for isolating solute aerosol particles from a helium nebulized LC eluent. The nebulized eluent passes through a heated cavity to evaporate the volatile solvent which results in lesser volatile solute aerosol particles. The aerosol particles are collimated at the exit of the heated cavity and emitted through a 0.5 mm aperture with the solvent vapor and helium nebulizing gas into a series of vacuum regions containing skimmers. The solute particles maintain a collimated beam along the axis of the skimmers due to their relatively high radial inertia. The solvent molecules and helium gas do not maintain the high degree of beam collimation, are excluded by the skimmers, and are pumped away by the vacuum system. The particles then impact the wall of the heated ion source resulting in flash vaporization and subsequent ionization. The use of skimmers in mass spectrometers is well-known in molecular beam applications and has been applied elsewhere to mass spectrometry analysis of aerosol particles (J. Allen, R. K. Gould, Rev. Sci. Instrum. 1981, 52, pp. 804–809).

Browner et al (R. F. Browner, A. W. Born, Anal. Chem. 1984, 56, pp. 875A–888A) describe a variety of aqueous sample introduction techniques for atomic spectroscopy which involve gas or ultrasonic nebulization. None of the approaches described are relevant to the present invention.

SUMMARY OF THE INVENTION

The apparatus may be generally described as an interface for use in a mass spectrometry system which vaporizes a liquid solution passing therethrough including first heating means; a fluid heat transfer means for transferring heat from the heating means to the sample stream; and means for transferring the solution into and vapor out of the heat transfer means; and wherein fluid in the heat transfer means is converted from a liquid to gas from the heating means and transfers energy to the liquid solution as the fluid changes from a gas to a liquid. Means for controlling the temperature of the heating means may also be used.

More particularly the apparatus for vaporizing and introducing a vaporized liquid solution into a spectrometer comprises a capillary tube having a first end and a second end; a fluid surrounding the capillary tube between the first and second ends; means for containing the fluid around the capillary tube; means for providing heat to the fluid; and wherein at least a portion of the fluid is in the liquid state.

Another less general description includes apparatus for vaporizing a liquid sample to be introduced into a mass spectrometer comprising, a capillary tube having inlet and outlet ends through which the liquid may flow and passing through a chamber having a metal wall disposed axially about the capillary, and sealing means at the input and output ends sealingly disposed between the metal wall and an outer wall of the capillary tube; a working fluid within the chamber; heating means disposed to heat the fluid within the chamber; an orifice in axial alignment with the outlet end of the capillary tube whereby a flow of vapor from the capillary is maintained; and wherein the working fluid, when liquid, fills only a portion of the chamber. Additional control means for controlling the temperature of the heating means may be used in all of the above. A fluid that has a heat of vaporization above 200 calories/gram is preferred such as water or a mixture of water and a surfactant.

The invention includes a process for vaporizing a liquid solution for introduction into a mass spectrometer the key features of which are: Heating a fluid in a chamber so as to vaporize at least a portion of the fluid; flowing the liquid solution through a capillary that passes through the chamber; and transferring energy to the liquid solution in a manner adapted to vaporize the solution by heat transfer from the vaporized fluid as the fluid changes from a gas to a liquid on an outer surface of the capillary.

DETAILED DESCRIPTION OF THE INVENTION

This invention is concerned with an apparatus and method for introduction of liquid solutions into a mass spectrometer. The objective is to utilize the invention as an interface between a liquid chromatograph and a mass spectrometer, or as a mass spectrometer inlet for direct sampling of liquid solutions. The invention may also be used as an interface for the introduction of standard solutions of known organic compounds for the purpose of calibrating a mass spectrometer used for real time monitoring of air, water, or a chemical process stream.

This invention is designed to transform liquid solutions into a vapor state prior to ionization by the mass spectrometer. It is particularly suitable for use as an LC/MS interface operating with conventional reverse phase (aqueous mobile phase) liquid chromatography at a flow rate of 1.0 ml/minute. This invention vaporizes the eluent of the LC without the need for subsequent aerosol desolvation. The vaporized solvent and solute may be ionized directly by atmospheric pressure ionization or chemical ionization. The solute may be isolated from the solvent vapor using conventional molecular beam techniques and ionized by electron impact, chemical ionization, photoionization or other means of ionizing compounds in a vacuum. This invention may also be used as a means of interfacing liquid chromatography or direct liquid sampling to other detection techniques such as ultraviolet, infrared, and atomic spectroscopy. The term liquid sample, liquid solution and eluent are used interchangeable herein. All refer to inputs to the apparatus of the invention and generally describe liquids containing other liquids or solids where one term is used the other may be understood to be equally usable.

The novel approach embodied by this invention uses high pressure vapor to transfer thermal energy to LC eluents flowing within a low thermal mass metal capillary. This thermal energy results in vaporization of the LC solvent while contained within the capillary. The vapor is obtained by heating a trapped volume of liquid (water) contained within a tubular metal chamber to an operating temperature of 130° to 180° C. The preferred versions use nickel or type 304 stainless steel as the material for the chamber. The preferred volume of water contained within the chamber is approximately 1 ml, however, the exact volume of water within the chamber is not critical. A low thermal mass metal capillary coaxially traverses the tubular chamber containing the trapped volume of water and steam. The metal capillary is sealed to the ends of the tubular chamber. The capillary is either thin wall gold nickel or other thermally conductive metal. Nickel is presently preferred for the capillary with an o.d. of 0.6 mm and i.d. of 0.35 mm. Gold may also be used. Other than the two points where it is sealed to the chamber, the capillary is not in physical contact with the chamber. The tubular chamber is heated by insulated resistance wire wrapped around and along the length of the chamber. One end of the metal capillary serves as an interface to the exit of an LC column (liquid eluent). The other end is the vapor exit which interfaces to the ion source of a mass spectrometer.

LC eluent entering the capillary results in a momentary reduction in local capillary temperature resulting in the near instantaneous condensation of steam on the outer wall of the capillary. Condensation continues as the device attempts to restore temperature equilibrium between the capillary and the steam. Condensation of steam results in rapid energy deposition to the metal capillary equivalent to the latent heat of vaporization of the condensed water. This energy deposition occurs primarily along that portion of the capillary in contact with liquid LC eluent. Changes in eluent flow or composition result in a shift in the location of steam condensation and eluent vaporization within the capillary accompanied by a greater or lesser rate of steam condensation. These changes are accommodated rapidly and automatically by the device while the heater power supply maintains a constant temperature of the trapped water reservoir. The constant temperature is maintained by a single thermocouple feedback temperature controller which controls power to the resistance heater. The thermocouple monitors the temperature of the tubular chamber in direct contact with the liquid phase of the trapped water reservoir. The response of the device to changing eluent flow or composition is much more rapid than the power response of the temperature controller due to the high energy capacity of the heated trapped water.

Water condensate on the outer wall of the capillary is removed by gravity and returns to the trapped liquid reservoir for revaporization to steam. Maximum efficiency is obtained by operating the device in an orientation other than horizontal, such that the condensed water on the capillary efficiently drains by gravity to the trapped liquid water reservoir and does not provide a significant insulating layer on the capillary. The present invention uses a small amount of surfactant added to the trapped water volume to assist in the flow of condensed water from the capillary. Cyclohexylamine, soap solutions, and other surfactants compatible with the metals may be used. The device is operated in a preferred orientation that is 30 to 90 degrees (angular measure) from horizontal. The properties of water or other condensible vapor for energy transfer are well-known and are often used to an advantage in devices known generically as "heat pipes". In this invention, the same physical property of the aqueous LC eluent (latent heat of vaporization) that limits many prior art LC/MS interfaces is utilized in reverse to provide vaporization of the LC eluent within the metal capillary without exposing the eluent vapor to excessive temperature.

Figure 1:
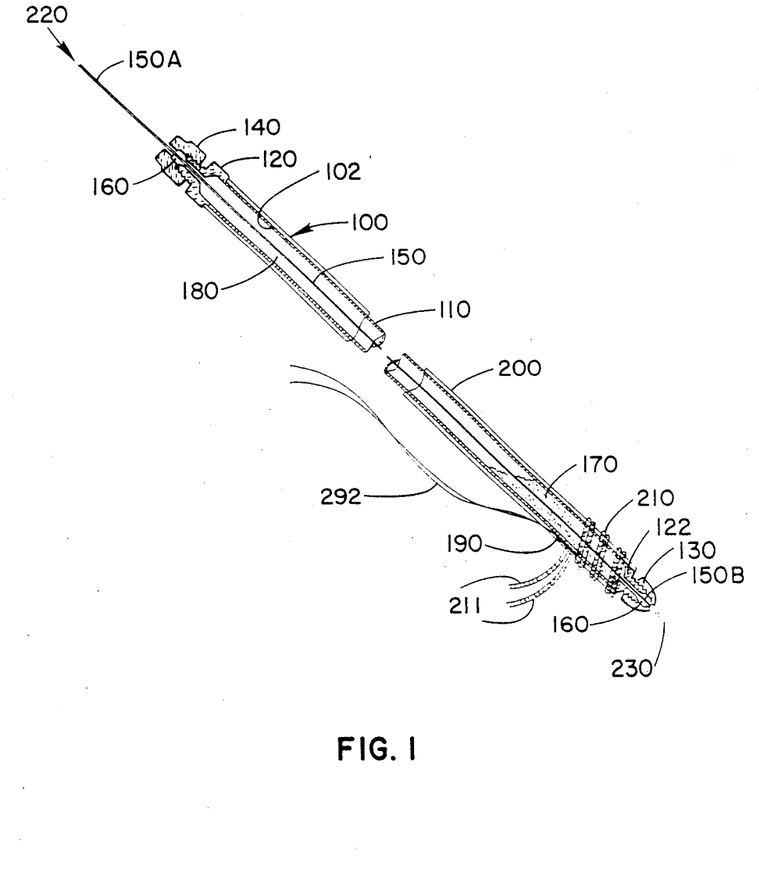
FIG. 1 depicts an exploded cutaway view of the LC/MS interface.

Referring now to FIG. 1 that shows an exploded view of the LC/MS interface 100. The trapped water chamber 102 of the interface 100 consists of a 22 cm length of thin wall nickel tubing 110 6.35 mm o.d. and 5.33 mm i.d. to each end of which are silver brazed commercially available 1/16" Swagelok ® compression fittings 120, 122. A modified Swagelok ® compression nut modified as an orifice 130 is fitted to fitting 122 at the vapor jet exit and of the interface 100 in order to reduce gaseous turbulence when used with atmospheric pressure ionization. An unmodified compression nut 140 is used on the inlet side of the device. A nickel capillary 150 traverses the length of the trapped water chamber 102 and is sealed to the chamber with 1/16" Teflon ferrules 160. The nickel capillary 150 in the present version of the interface is 0.60 mm o.d. and 0.35 mm i.d. (0.12 mm wall thickness). The liquid phase of the trapped water 170 rests at the bottom of the chamber in equilibrium with the vapor phase 180 at a normal operating temperature of 160° C. The temperature of the nickel tubing 110 in direct contact with the liquid phase of the trapped water is monitored with a sheathed thermocouple 190 having leads 192, shown in FIG. 1 as an unsheathed version for visual clarity. While a single walled chamber will work, a slotted copper sheath 200 preferentially surrounds the nickel tubing 110 in order to provide temperature uniformity and additional strength along the length of the chamber 102. Approximately 4.1 meters of 7 ohm per foot insulated resistance wire 210 having leads 211 was wrapped over the entire length of the copper sheath 200 in order to provide thermal energy to the trapped water 170. The extended inlet portion of the nickel capillary 150 is normally attached directly to a liquid chromatographic column or other input device (not shown). The entire volume of liquid solution from the column (usually an aqueous solvent with chromatographically separated solute components at approximately 1 ml/min) enters the capillary at inlet 220 and is transported to that portion of the capillary in contact with the equilibrium vapor phase of the heated trapped water 180. The exiting vapor 230 is then directed to the ion source of a mass spectrometer.

Since the liquid solution entering the apparatus is normally room temperature (always lower in temperature than the trapped water vapor), the trapped water vapor condenses on the cooled portion of the capillary in contact with liquid solution. Much less condensation (energy deposition) occurs on that region of the capillary containing vaporized eluent. The trapped water vapor rapidly condenses on the surface to the capillary 150 releasing latent heat of vaporization to the capillary 150. The process of condensation results in a momentary reduction in pressure above the surface of the trapped liquid phase. The trapped liquid phase volatilizes, by absorbing thermal energy from the resistance heater, in order to reestablish the trapped liquid-vapor equilibrium for the constant operating temperature. The low thermal mass capillary 150 transfers the latent heat (condensation) energy by thermal conduction to the liquid solution resulting in rapid volatilization of the solution.

It is presumed that the liquid solution passes through a aerosol stage in the process of vaporization. Room light visual examination of the exit of the capillary discharged into laboratory air, operating at 160° C. 1 ml/min aqueous flow, does not reveal the presence of an aerosol in the immediate vicinity of the capillary exit. A diffuse aerosol is observed a few cm downstream of the capillary exit due to mixing and condensation with cooler laboratory air. Illumination of the region 5 mm downstream of the capillary exit with a 5 mW Helium Neon laser fails to produce an image indicative of an aerosol when viewed perpendicular to the laser beam. Occasionally, a faint narrow image is observed when the capillary exit region is viewed oblique to the laser beam. This image may be due to a very small population of superheated aerosol droplets that escape desolvation in the current version of the interface.

A more general description of the interface apparatus 100 than the specific example of the above described embodiment includes first a chamber 102 that is partially filled with a liquid. Preferred liquids include those having heats of vaporization above 200 calories/gram, although water appears to be the best liquid to use. The chamber has walls 110 of metal that are preferably nickel although other metals with good thermal conductivity and strength such as stainless steel and the like may be used. The chamber walls 110 may be of the aforementioned metals only or may have a sheath 200 of metal (e.g. copper) as an outer layer. This outer layer should have very good thermal conductivity. A capillary tube 150 passes through the chamber 100, having its outer surface in sealing relationship with the chamber wall 110 at ends 150A and 150B. Compression fittings 120. 122 or other equivalent seal known to those skilled in the art may be used. Depending on the, method of sealing used compression nuts and ferrules may not be needed. For purposes of the invention the particular method of sealing is not critical as long as a good seal that can withstand high pressures generated by the vapor in the apparatus 100 can be contained.

Figure 2:
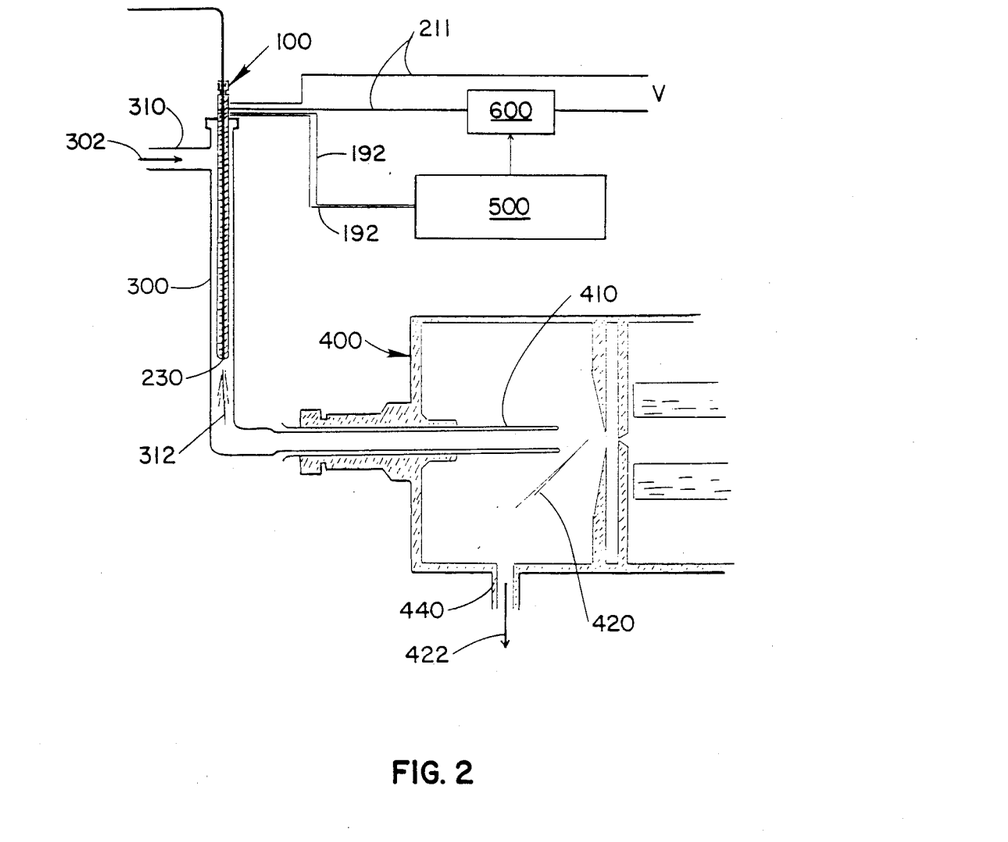
FIG. 2 depicts the use of the LC/MS interface together with an atmospheric pressure ionization tandem mass spectrometer.

A typical configuration of the interface with an atmospheric pressure ionization TAGA 6000E tandem mass spectrometer is shown in FIG. 2. The interface 100 is positioned coaxially within a heated 22 mm o.d. pyrex tube 300 which serves as the transfer line for dilution air 302 entering at inlet 310. The flow rate of dilution air is nominally 10-30 liters/minute. The dilution air 302 is required in order to obtain the desired ionization mode in the atmospheric pressure ion source, and to minimize the residence time of the gas in the relatively large volume of the ionizer. The pyrex tube 300 is heated with conventional heat tape (not shown) to a nominal temperature of 150° C. in order to prevent recondensation of the vaporized solute or solvent. Diluted vapor 312 passes into the ionization region of a commercially available tandem mass spectrometer 400 through a double wall glass transfer line 410. Ionization on this particular mass spectrometer occurs through interaction of reagent ions in the air with the solute molecules. A population of reagent ions is maintained with a high voltage corona discharge 420. Ions are then transported into the high vacuum region of the mass spectrometer. Air and eluent vapor 422 are continually drawn out of the atmospheric pressure ionizer region 430 at outlet 440.

Temperature control of the interface 100 is maintained with a solid state temperature controller 500 which monitors the thermocouple 190 attached to the interface 100 through leads 192. The thermocouple 190 is preferentially mounted at the level of the liquid 170. The temperature controller 500 activates a zero-crossing solid state relay 600 (or other electrical control) which controls the application of electrical power through leads 211 to the resistance heater 210 of the interface. Sufficient electrical power is supplied to maintain the interface 100 at a selectable constant temperature (usually 160° C.). The liquid solution enters the interface via inlet 220 and is transformed to vapor 230 prior to dilution with air 302 and ionization.

EXAMPLES 1-5

Figure 3:
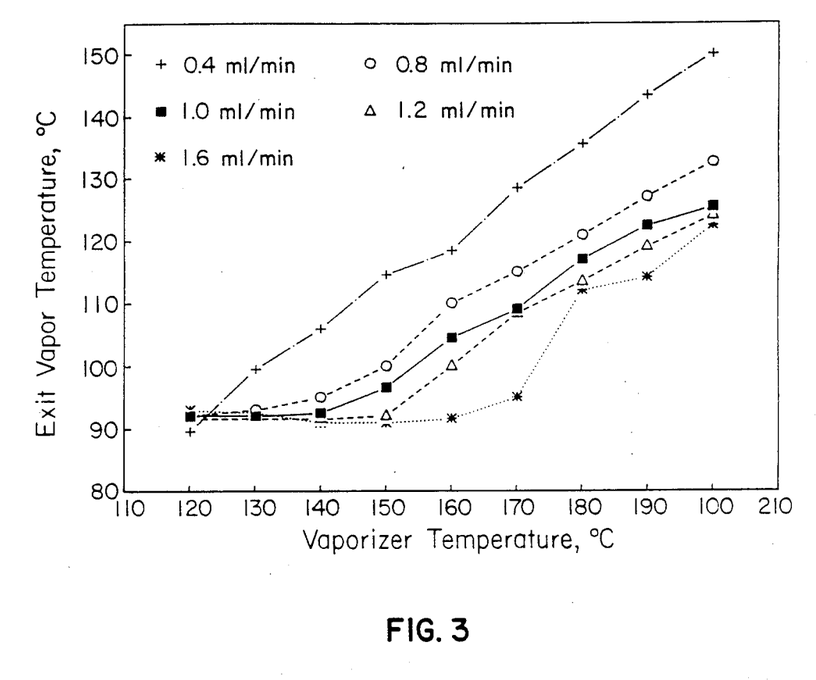
FIG. 3 shows a plot of vaporization temperature versus exit vapor temperature at five different flow rates.

The experimentally determined relationship between exit vapor temperature at atmospheric pressure and the temperature of the trapped water is shown in FIG. 3 for five aqueous flow rates. The vapor temperatures shown in FIG. 3 were measured at a point 2 mm beyond the capillary exit with a thermocouple constructed from crossed 0.003" diameter chromel and alumel wires spot welded at the junction. The actual temperature of the eluent vapor may be slightly higher (a few degrees) than that indicated in FIG. 3 since the jet core near the exit of the capillary is less than 1 mm in diameter, and may contain entrained cooler air at the surface.

As the temperature of the trapped water in the vaporizer increases, the exit vapor contains solvent aerosol which moderates the temperature rise of the vapor as illustrated in FIG. 3 for flows greater than 0.4 ml/min. The vapor temperature increases significantly when virtually complete desolvation of the aerosol occurs within the capillary. Following the onset of virtually complete vaporization, the exit gas temperature increases with increasing vaporizer temperature. This temperature rise is due to vaporization occurring at an increasing distance within and from the exit of the capillary. For a given flow rate, the point of vaporization extends further into the capillary with increasing trapped water temperature since the higher steam temperature provides an increased rate of energy deposition to the capillary 150, resulting in earlier vaporization than at lower temperatures. The increase in eluent vapor temperature is due, in part, to the increase in pressure (resulting in an increase in boiling point) within the capillary 150 as a result of the capillary resistance to vapor flow. The vaporizer temperature exhibits significant fluctuation at flow rates above 1.3 ml/min. which may be the cause of the erratic temperature rise shown in FIG. 3 for a flow rate of 1.6 ml/min. At this eluent flow rate, the 1 ml of trapped water is extremely active, completing the cycle from liquid to vapor and back to liquid in significantly less than 1 minute. It is presumed that the temperature instability of the vaporizer is caused by superheating and cavitation of the trapped water volume resulting in part from the small surface area of the liquid trapped water in the tubular chamber. This does not represent a limit to the principle of operation but rather to the particular dimensions and geometry of the present device. A larger diameter chamber will alleviate this phenomenon allowing temperature regulation at higher eluent flow rates. A larger, for example 7.7 mm i.d. stainless steel (type 304) tubing is preferred for larger flow rates which will approximately double the surface area of the liquid trapped water.

EXAMPLES 6-8

In order to evaluate the new device as an LC/MS interface, a liquid chromatograph consisting of a Varian model 5000 HPLC gradient pump and a Dupont C18 Zorbax chromatographic column was configured. The interface was attached to the exit of the column and interfaced to a Sciex TAGA 6000E tandem mass spectrometer. 20 ul of a 50 ppm standard of selected explosives was injected onto the HPLC column. Chromatographic conditions consisted of a methanol:water gradient (40–80 percent methanol) at a constant flow rate of 1.0 ml/min as shown in FIG. 4b. The interface temperature was fixed at 160° C. throughout the analysis. The thermally labile explosives of interest were RDX, nitroglycerine, and PETN. These compounds fragment extensively in the TAGA APCI ion source resulting in extensive distribution of negative ion charge between the fragment masses. Nitroglycerine and PETN are aliphatic nitrates which generate an $NO_3-$ anion at m/z 62. RDX is a nitroaromatic which generates an $NO_2-$ anion at m/z 46. The TAGA was programmed to alternate in a selected ion monitoring fashion between m/z 62 and m/z 46 throughout the entire LC/MS experiment.

Figure 4A:
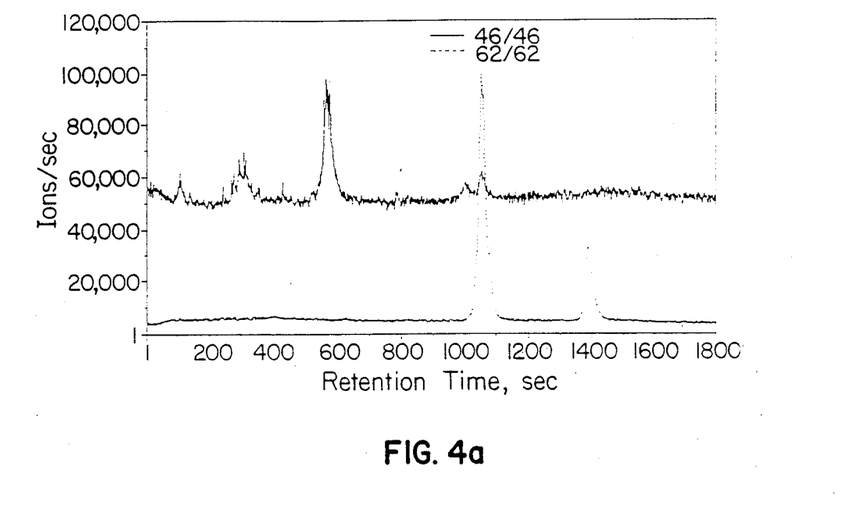
FIG. 4a depicts a negative ion LC/MS chromatogram from 20 µl of a 50 ppm standard containing RDX, nitroglycerine, and PETN using a gradient elution technique.
Figure 4B:
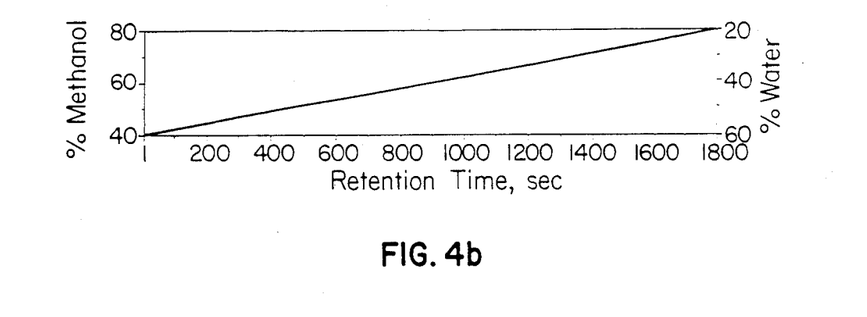
FIG. 4b depicts the elution gradient using a methanol/water mixture.

The resulting LC/MS chromatogram is shown in FIG. 4a. The LC peaks for the target analytes are clearly evident. The Varian HPLC pump is an older version single piston apparatus which generates significant pulsing in the HPLC eluent. The most widely used LC/MS interface (Thermospray) is very sensitive to pulsing effects which result in a distorted and multiply split appearance to the chromatographic peaks, which may impair the ability to perform quantitative analysis. No distortion or splitting is evident in the chromatogram of FIG. 4a confirming the unique ability of this interface to rapidly deposit energy on demand to accommodate variations in HPLC eluent flow.

EXAMPLE 9

Figure 5A:
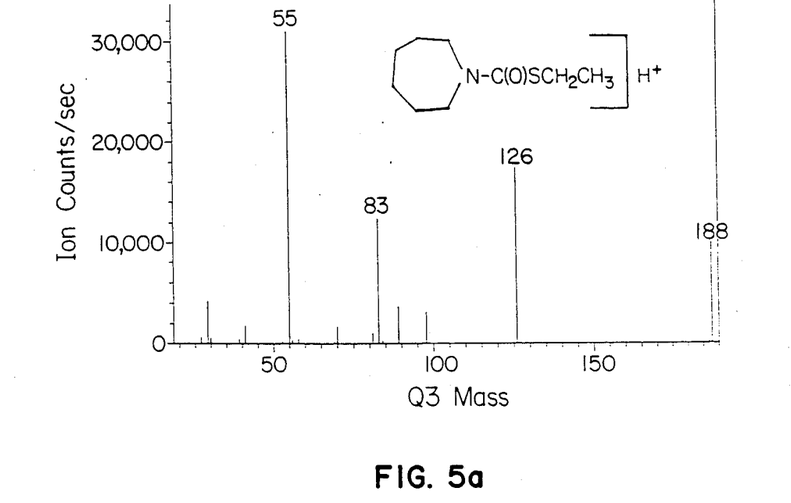
FIG. 5a illustrates a positive ion daughter spectrum for the rice herbicide Molinate (Ordram).
Figure 5B:
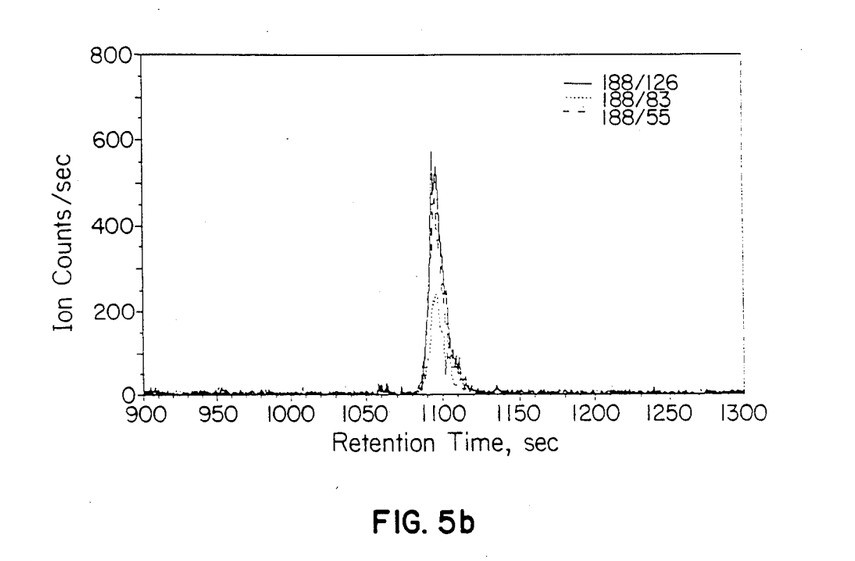
FIG. 5b illustrates a positive ion LC/MS/MS chromatogram for Molinate.

FIG. 5a illustrates a positive ion daughter spectrum. FIG. 5b illustrates an LC/MS/MS chromatogram for the rice herbicide Molinate for parent daughter ion pairs having a parent m/z = 188 and daughter m/z's of 126, 83, and 55. The daughter spectrum and LC/MS/MS data were obtained at 22 eV (Lab) collision energy with an argon target thickness of $3.5 \times 10^{14} cm^{-2}$ (indicated). The chromatographic peak was obtained from a 100 ul injection of a methanol standard containing 0.11 ug/ml of molinate, using gradient chromatographic conditions identical to those for the explosives.

This invention offers the following advantages:

(1) Virtually complete vaporization occurs at relatively low temperatures within the capillary. Water as an LC solvent is particularly difficult to transform into a gas due to its high latent heat of vaporization. Desolvation of aqueous aerosols requires ordinarily exposure of the vapor and aerosol to temperatures on the order of 300° C.

(2) The temperature within the metal capillary is more uniform. Temperature sensitive analyte molecules are not exposed to "hot spots", which may induce degradation of the analytes. The temperature of the region between the exit of the invention and the point of ionization need only be maintained between 100–150 degrees C. to prevent condensation of the gaseous LC eluent (water). This temperature is generally less than the aerosol desolvation region temperature of other LC/MS interfaces, particularly when water is used as the mobile phase.

(3) Ease of control. Binary solvent systems such as acetonitrile/water or methanol/water are often used in reverse phase LC in which the composition of the solvent mixture is gradually changed during the course of analysis. This invention can accommodate 0-100 percent acetonitrile:water and methanol:water gradients at a flow rate of 1 ml/minute without exposure of the liquid or vapor eluent to a temperature in excess of 160° C.

(4) The invention is insensitive to variations in liquid flow up to approximately 1.3 ml/min. Variations generally result from "pulsing" of the LC pumping system. This invention is better capable of rapidly depositing extra energy "on demand" to the LC eluent without requiring an excessive temperature.

(5) The particular property of aqueous solvents (high latent heat of vaporization) that often presents difficulties in the design of an LC/MS interface is used in reverse by this invention to compensate for this property of the LC eluent and eliminate the need for excessive temperatures.

(6) The invention has been used with an atmospheric pressure ion source tandem mass spectrometer (Sciex TAGA). It can be adapted to practically any mass spectrometer having an API or CI ion source and sufficient pumping capacity for the gas loads generated by the device.

(7) The invention is easy to use since gradient and flow changes are accommodated without changes in operating temperature. The interface requires practically no tuning or adjustments in order to produce satisfactory results.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. An apparatus for use in a mass spectrometry system which vaporizes an eluent passing therethrough comprising:
   a. first heating means;
   b. fluid heat transfer means for transferring heat from the heating means to the eluent;
   c. means for transferring the eluent into and vapor out of the heat transfer means; and wherein a working fluid in the heat transfer means is converted from a liquid to a gas by the heating means and transfers energy to the eluent as the working fluid changes from a gas to a liquid.

2. The apparatus of claim 1 further comprising control means for controlling the temperature of the heating means.

3. The apparatus of claim 1 wherein the working fluid has a heat of vaporization above 200 calories/gram.

4. The apparatus of claim 1 wherein the working fluid is water.

5. The apparatus of claim 1 wherein the working fluid is a mixture of water and a surfactant.

6. The apparatus of claim 1 wherein the fluid heat transfer means comprises a chamber partially filled with working fluid in the liquid phase.

7. The apparatus of claim 1 wherein the means for transferring the eluent comprises a capillary.

8. The apparatus of claim wherein the first heating means comprises a resistance wire.

9. The apparatus of claim 2 wherein the control means comprises a temperature controller attached to the thermocouple that controls a relay that controls power to the heating means.

10. The apparatus of claim 1 further comprising temperature sensing means.

11. An apparatus for vaporizing and introducing a vaporized eluent into a spectrometer comprising:
   a. a capillary tube having a first end and a second end;
   b. a working fluid surrounding the capillary tube between the first and second ends;
   c. means for permanently containing the working fluid around the capillary tube, wherein the means for containing the working fluid around the capillary tube comprises a wall in sealed relationship with the outer surface of the first and second ends of the capillary that defines a chamber containing the working fluid; and
   d. means for providing heat to the working fluid.

12. The apparatus of claim 11 further providing control means for controlling the temperature of the working fluid.

13. The apparatus of claim 11 wherein the working fluid has a heat of vaporization above 200 calories/gram.

14. The apparatus of claim 11 wherein the working fluid is water.

15. The apparatus of claim 11 wherein the working fluid is a mixture of water and a surfactant.

16. The apparatus of claim 11 wherein the capillary and wall are of nickel.

17. The apparatus of claim 11 wherein the wall has an outer sheath.

18. The apparatus of claim 17 wherein the sheath is copper.

19. The apparatus of claim 11 further comprising temperature sensing means.

20. Apparatus for vaporizing an eluent to be introduced into a mass spectrometer comprising:
   a. a capillary tube having inlet and outlet ends through which the eluent may flow, the capillary tube passing through a chamber having a metal wall disposed coaxially about the capillary and sealing means at the input and output ends sealingly disposed between the metal wall and an outer wall of the capillary tube to form a sealed coaxial chamber about the capillary;
   b. a working fluid within the chamber that is in both the liquid and gas phases and the liquid phase fills only a portion of the chamber;
   c. heating means disposed to heat the fluid within the chamber; and
   d. an orifice in axial alignment with the outlet end of the capillary tube whereby a flow of vapor from the capillary is maintained.

21. The apparatus of claim 20 further comprising control means for controlling the temperature of the heating means.

22. The apparatus of claim 20 wherein the working fluid has a heat of vaporization above 200 calories/gram.

23. The apparatus of claim 20 wherein the working fluid is water.

24. The apparatus of claim 20 wherein the working fluid is a mixture of water and a surfactant.

25. The apparatus of claim 20 further comprising a sheath of metal axially disposed about the metal wall.

26. The apparatus of claim 25 wherein the capillary consists of nickel, stainless steel, or gold; the metal wall consists of nickel or stainless steel; and the sheath consists of copper.

27. The apparatus of claim 21 further comprising temperature sensing means.

28. A process for vaporizing an eluent for introduction into a mass spectrometer comprising:
 a. heating a working fluid in a sealed chamber so as to vaporize at least a portion of the fluid; and
 b. transferring energy to the eluent in a manner adapted to vaporize the eluent by heat transfer from the vaporized working fluid as the working fluid changes from a gas to a liquid.

* * * * *

UNITED STATES PATENT AND TRADEMARK OFFICE
CERTIFICATE OF CORRECTION

PATENT NO. : 4,982,097
DATED : January 1, 1991
INVENTOR(S) : Laurence E. Slivon, Donald V. Kenny, and Richard A. Severance It is certified that error appears in the above—identified patent and that said Letters Patent is hereby corrected as shown below:

Sheet 3 of Drawings, Fig. 3, in the abcissa, Vaporizer Temperature, "100" should be -- 200 --.

Signed and Sealed this

Twenty-eighth Day of July, 1992

Attest:

DOUGLAS B. COMER

Attesting Officer

Acting Commissioner of Patents and Trademarks